US008048639B2

(12) United States Patent
Dotan et al.

(10) Patent No.: US 8,048,639 B2
(45) Date of Patent: Nov. 1, 2011

(54) METHOD FOR EVALUATING RISK IN MULTIPLE SCLEROSIS

(75) Inventors: Nir Dotan, Shoham (IL); Avinoam Dukler, Moddin (IL); Jennifer Yarden, Moshav Maor (IL)

(73) Assignee: Glycominds Ltd., Modi'in (IL)

( * ) Notice: Subject to any disclaimer, the term of this patent is extended or adjusted under 35 U.S.C. 154(b) by 73 days.

(21) Appl. No.: 12/704,257

(22) Filed: Feb. 11, 2010

(65) Prior Publication Data

US 2010/0227337 A1    Sep. 9, 2010

Related U.S. Application Data

(60) Provisional application No. 61/152,168, filed on Feb. 12, 2009.

(51) Int. Cl.
*G01N 33/53* (2006.01)
*A61B 5/05* (2006.01)

(52) U.S. Cl. .............. 435/7.1; 435/2; 600/410; 600/420

(58) Field of Classification Search .................. None
See application file for complete search history.

(56) References Cited

U.S. PATENT DOCUMENTS

| | | | |
|---|---|---|---|
| 5,030,560 | A | 7/1991 | Sinor et al. |
| 6,972,172 | B2 | 12/2005 | Dukler et al. |
| 7,537,900 | B2 | 5/2009 | Dotan et al. |
| 7,572,592 | B2 | 8/2009 | Dotan et al. |
| 7,906,291 | B2 * | 3/2011 | Dotan et al. ............ 435/7.1 |
| 2004/0077023 | A1 | 4/2004 | Dotan et al. |
| 2004/0241763 | A1 | 12/2004 | Dotan et al. |
| 2006/0172338 | A1 | 8/2006 | Dotan et al. |
| 2006/0234301 | A1 | 10/2006 | Dotan et al. |

FOREIGN PATENT DOCUMENTS

| | | |
|---|---|---|
| JP | 02151765 A | 6/1990 |
| JP | 02161357 A | 6/1990 |
| WO | WO-0049412 A1 | 8/2000 |
| WO | WO-0114881 A1 | 3/2001 |
| WO | WO-0151207 A1 | 7/2001 |
| WO | WO-0218950 A1 | 3/2002 |
| WO | WO-02064556 A2 | 8/2002 |
| WO | WO-03000733 A2 | 1/2003 |
| WO | WO-2004015420 A1 | 2/2004 |
| WO | 2004034031 A2 | 4/2004 |
| WO | WO-2004077023 A2 | 9/2004 |
| WO | WO-2006/117689 A2 | 11/2006 |

OTHER PUBLICATIONS

Freedman, "Anti-alpha-glucose-based Glycan IgM Antibodies in Patients with a Clinically Isolated Syndrome: Analyses from the Betaferon in Newly Emerging Multiple Sclerosis for Initial Treatment (BENEFIT) Study", ECTRIMS, Aug. 27, 2009.
Dotan N. et al., "Anti-glycan antibodies as biomarkers for diagnosis and prognosis" Lupus, Basingstoke, GB, 15 (7):442-450 (2006).
Dalton et al., "Application of the new McDonald Criteria to Patients with Clinically Isolated Syndromes Suggestive of Multiple Sclerosis", *Ann. Neurol.*, 52:47-53 (2002).
Alberts et al. "Sugars Are Food Molecules of the Cell", in *Molecular Biology of the Cell*, Garland Publishing Inc., New York & London, pp. 50-51 (1983).
Banin et al., "A Novel Linear Code® Nomenclature for Complex Carbohydrates", *Trends Glycoscience Glycotech.*, 14(77):127-137 (2002).
Bao, J. J., "Capillary electrophoretic immunoassays", *J. Chromatogr. B.*, 699:463-480 (1997).
Bergamaschi, R., "Prognostic Factors in Multiples Sclerosis", *Int. Rev. Neurobiol.*, 79:423-447 (2007).
Berger et al., "Antimyelin Antibodies as a Predictor of Clinically Definite Multiple Sclerosis after a First Demyelinating Event", *N. Engl. J. Med.*, 349(2):139-145 (2003).
Binder et al., "The role of natural antibodies in atherogenesis", *J. Lipid Res.*, 46:1353-1363 (2005).
Boneschi et al., "Mitoxantrone for multiple sclerosis", *Cochrane Database of Systematic Rev.*, 4:CD002127 (2005).
Bozzaro et al., "Monoclonal Antibodies against *Dictyostelium* Plasma Membranes: their Binding to Simple Sugars", *Cell Differentiation*, 17:83-94 (1985).
Brex et al., "A Longitudinal Study of Abnormalities on MRI and Disability From Multiple Sclerosis", *N. Engl. J. Med.*, 346 (3):158-164 (2002).
Brusaferri et al., "Steroids for multiple sclerosis and optic neuritis: a meta-analysis of randomized controlled clinical trials", *J. Neurol.*, 247(6):435-442 (2000).
Carotenuto et al., "Conformational Analysis of a Glycosylated Human Myelin Oligodendrocyte Glycoprotein Peptide Epitope Able to Detect Antibody Response in Multiple Sclerosis", *J. Med. Chem.*, 44:2378-2381 (2001).
Comi et al., "Effect of early interferon treatment on conversion to definite multiple sclerosis: a randomised study", *Lancet*, 357(9268):1576-1582 (2001).
Confavreux et al., "Early clinical predictors and progression of irreversible disability in multiple sclerosis: an amnesic process", *Brain*, 126:770-782 (2003).
Dovio et al., "Immediate Fall of Bone Formation and Transient Increase of Bone Resorption in the Course of High-Dose, Short-Term Glucocorticoid Therapy in Young Patients with Multiple Sclerosis", *J. Clin. Endocrinol. Metab.*, 89(10):4923-4928 (2004). Durelli et al., "MRI activity and neutralising antibody as predictors of response to interferon beta treatment in multiple sclerosis", *J. Neurol. Neurosurg. Psychiatry.*, 79:646-651 (2008).
Felici et al., "Phage-Displayed Peptides as Tools for Characterization of Human Sera", *Meth. Enzymol.*, 267:116-129 (1996).
Fisniku et al., "Disability and $T_2$ MRI lesions: a 20-year follow-up of patients with relapse onset of multiple sclerosis", *Brain*, 131:808-817 (2008).
Freedman et al., "Anti-α-glucose-based glycan IgM antibodies predict relapse activity in multiple sclerosis after the first neurological event", *Multiple Sclerosis*, 15:422-430 (2009).
Freedman et al., "Recommended Standard of Cerebrospinal Fluid Analysis in the Diagnosis of Multiple Sclerosis", *Arch. Neurol.*, 62:865-870 (2005).
Gonsette, R.E., "Compared benefit of approved and experimental immunosuppressive therapeutic approaches in multiple sclerosis", *Exp. Opin. Pharmacother.*, 8(8):1103-1116 (2007).
Gyorgy et al., "Natural autoantibodies reactive with glycosaminoglycans in rheumatoid arthritis", *Arthritis Res. Ther.*, 10(5):1-12 (2008).

(Continued)

*Primary Examiner* — Ali R. Salimi
*Assistant Examiner* — Stephen Gucker
(74) *Attorney, Agent, or Firm* — Mintz Levin Cohn Ferris Glovsky and Popeo, P.C.; Ivor R. Elrifi; Ingrid A. Beattie (57) ABSTRACT

The invention relates to methods and reagents for diagnosing and assessing the prognosis of multiple sclerosis.

4 Claims, 4 Drawing Sheets

OTHER PUBLICATIONS

Holme et al., "Structural Studies on the O-Specific Side-Chains of the Cell-Wall Lipopolysaccharide from *Salmonella typhimurium* 395 MS", *Carbohydr. Res.*, 8:43-55 (1968).

Hou et al., "Development of Peptide Mimotopes of Lipooligosaccharide from Nontypeable *Haemophilus influenzae* as Vaccine Candidates", *J. Immunol.*, 170:4373-4379 (2003).

International Search Report for PCT/IB2003/03878, mailed Jan. 9, 2004.

International Search Report for PCT/IB2006/001666, mailed Nov. 8, 2006.

Jacobs et al., "Correlation of Clinical, Magnetic Resonance Imaging, and Cerebrospinal Fluid Findings in Optic Neuritis", *Ann. Neurol.*, 41(3):392-398 (1997).

Jacobs et al., "Intramuscular Interferon Beta-1a Therapy Initiated During a First Demyelinating Event in Multiple Sclerosis", *N. Engl. J. Med.*, 343(13):898-904 (2000).

Johnson, K. P., "Control of multiple sclerosis relapses with immunomodulating agents", *J. Neurol. Sci.*, 256(Suppl. 1):S23-S28 (2007).

Kappos et al., "Effect of early versus delayed interferon beta-1b treatment on disability after a first clinical event suggestive of multiple sclerosis: a 3-year follow-up analysis of the BENEFIT study", *Lancet*, 370(9585):389-397 (2007).

Kuhle et al., "Lack of Association between Antimyelin Antibodies and Progression to Multiple Sclerosis", *N. Engl. J. Med.*, 356:371-378 (2007).

Kurtzke, J. F., Rating neurologic impairment in multiple sclerosis: An expanded disability status scale (EDSS), *Neurol.*, 33(11):1444-1452 (1983).

Leary et al., "Primary Progressive Multiple Sclerosis Current and Future Treatment Options", *CNS Drugs*, 19(5):369-376 (2005).

Lolli et al., "An N-glucosylated peptide detecting disease-specific autoantibodies, biomarkers of multiple sclerosis", *Proc. Natl. Acad. Sci. U.S.A.*, 102(29):10273-10278 (2005).

Lolli et al., "The glycopeptides CSF114(Glc) detects serum antibodies in multiple sclerosis", *J. Neuroimmunol.*, 167:131-137 (2005).

Mandrioli et al., "A multifactorial prognostic index in multiple sclerosis. Cerebrospinal fluid IgM oligoclonal bands and clinical features to predict the evolution of the disease", *J. Neurol.*, 255:1023-1031 (2008).

Martinelli et al., "Mitoxantrone for multiple sclerosis", *Cochrane Database System Reviews*, (4):CD002127 (2005).

Matsuda, et al., "Antibody Response to Haptenic Sugar Antigen: Immunodominancy of Protein-Bound Lactose Formed by Amino-Carbonyl Reaction", *Mol. Immun.*, 24(5):421-425 (1987).

Mazzucco et al., "A Synthetic Glycopeptide of Human Myelin Oligodendrocyte Glycoprotein to Detect Antibody Responses in Multiple Sclerosis and Other Neurological Diseases", *Bioorg. Med. Chem. Lett.*, 9:167-172 (1999).

McDonald et al., "Recommended Diagnostic Criteria for Multiple Sclerosis: Guidelines from the International Panel on the Diagnosis of Multiple Sclerosis", *Ann. Neurol.*, 50(1):121-127 (2001).

Miller et al., "Differential diagnosis of suspected multiple sclerosis: a consensus approach", *Multiple Sclerosis*, 14:1157-1174 (2008).

Miller, D. H., "Biomarkers and Surrogate Outcomes in Neurodegenerative Disease: Lessons from Multiple Sclerosis", *NeuroRx*, 1:284-294 (2004).

Munari et al., "Therapy with glatiramer acetate for multiple sclerosis", *Cochrane Database of Systematic Rev.*, 4:CD004678 (2003).

Murray, T. J., "The cardiac effects of mitoxantrone: do the benefits in multiple sclerosis outweigh the risks?", *Exp. Opin. Drug Safety*, 5(2):265-274 (2006).

O'Riordan et al., "The prognostic value of brain MRI in clinically isolated syndromes of the CNS", *Brain*, 121:495-503 (1998).

Papini et al., "[Asn$^{31}$(N-β-D-Glucopyranosyl)]hMOG(30-50): An Antigen to Identify Anti-hMOG Peptide Antibodies in Multiple Sclerosis Patients", *Proceedings of the 10$^{th}$ International Congress of Immunology*, Monduzzi Editore, pp. 1239-1244 (1998).

Patent Abstracts of Japan for Japanese Laid-Open Publication No. 02-161357, published Jun. 21, 1990.

Perrin et al., "A National Survey of Physician Perspectives of the Unmet Needs in the Treatment of Multiple Sclerosis", *JMCP*, 15(7):572-573 (2009) (Abstract Only).

Pirko et al., "A human antibody that promotes remyelination enters the CNS and decreases lesion load as detected by T2-weighted spinal cord MRI in a virus-induced murine model of MS", *FASEB J.*, 18:1577-1579 (2004).

Pittock et al., "Clinical Implications of Benign Multiple Sclerosis: A 20-Year Population-Based Follow-up Study", *Ann. Neurol.*, 56:303-306 (2004).

Polman et al., "Diagnostic Criteria for Multiple Sclerosis: 2005 Revisions to the 'McDonald Criteria'", *Ann. Neurol.*, 58:840-846 (2005).

Poser et al., "New Diagnostic Criteria for Multiple Sclerosis: Guidelines for Research Protocols", *Ann. Neurol.*, 13:227-231 (1983).

Rice et al., "Interferon in relapsing-remitting multiple sclerosis", *Cochrane Database of Systematic Rev.*, 4:CD002002 (2001).

Rio et al., "Relationship between MRI lesion activity and response to IFN-beta in relapsing-remitting multiple sclerosis patients", *Mult. Scler.*, 14:479-484 (2008).

Ritchie et al., "Reference Distributions for Immunoglobulins A, G, and M: A Practical, Simple, and Clinically Relevant Approach in Large Cohort", *J. Clin. Lab. Anal.*, 12:363-370 (1998).

Rongen et al., "Liposomes and immunoassays", *J. Immunol. Meth.*, 204(2):105-133 (1997).

Rudick et al., "Current approaches to the identification and management of breakthrough disease in patients with multiple sclerosis", *Lancet Neurol.*, 8:545-559 (2009).

Ruggieri et al., "Glatiramer Acetate in Multiple Sclerosis: A Review", *CNS Drug Rev.*, 13(2):178-191 (2007).

Saveliev et al., "Amylolytic Activity of IgM and IgG Antibodies from Patients with Multiple Sclerosis", *Immun. Letters*, 86:291-297 (2003).

Schmalzing et al., "Capillary electrophoresis bases immunoassays: A critical review", *Electrophoresis*, 18:2184-2193 (1997).

Schwarz et al., "A new kind of carbohydrate array, its use for profiling antiglycan antibodies, and the discovery of a novel human cellulose-binding antibody", *Glycobiol.*, 13(11):749-754 (2003).

Schwarz et al., "Serum anti-Glc($\alpha$1,4)Glc($\alpha$) antibodies as a biomarker for relapsing-remitting multiple sclerosis", *J. Neurol. Sci.*, 244:59-68 (2006).

Self et al., "Advances in immunoassay technology", *Curr. Opin. Biotechnol.*, 7:60-65 (1996).

Simone et al., "Course and prognosis in early-onset MS. Comparison with adult-onset forms", *Neurol.*, 59(12):1922-1928 (2002).

Sormani et al., "Modelling MRI enhancing lesion counts in multiple sclerosis using a negative binomial model: implications for clinical trials", *J. Neurol. Sci.*, 163(1):74-80 (1999).

Steinman, L., "Multiple sclerosis: a two-stage disease", *Nature Immunol.*, 2(9):762-764 (2001).

Stryer, L., *Biochemistry*, 4$^{th}$ Edition, W.H. Freeman and Company, New York, NY, pp. 472-473 (1995).

Tintore et al., "Baseline MRI predicts future attacks and disability in clinically isolated syndromes", *Neurol.*, 67:968-972 (2006).

Uttner et al., "Reversible impaired memory induced by pulsed methylprednisolone in patients with MS", *Neurol.*, 64(11):1971-1973 (2005).

van Horssen et al., "Extensive extracellular matrix depositions in active multiple sclerosis lesions", *Neurobiol. Dis.*, 24:484-491 (2006).

Vollmer, T., "The natural history of relapses in multiple sclerosis", *J. Neurol. Sci.*, 256(Suppl. 1):S5-S13 (2007).

Warrington et al., "A Recombinant Human IgM Promotes Myelin Repair After a Single, Very Low Dose", *J. Neurosci. Res.*, 85:967-976 (2007).

Weinshenker et al., "The Natural History of Multiple Sclerosis: A Geographically Based Study", *Brain*, 112:1419-1428 (1989).

Yarden and Dotan, "Anti-Collagen IV IgM and anti-Glc(a1,2)Gal(b) (GAAB) IgM can be used for differentiation between Relapsing Remitting Multiple sclerosis (RRMS) patients and patients having other neurological diseases (OND)", Jul. 1, 2009.

Zhan et al., "A Peptide Mimetic of G-$\alpha$1,3-Gal is Able to Block Human Natural Antibodies", *Biochem. Res. Commun.*, 308(1):19-22 (2003).

* cited by examiner

METHOD FOR EVALUATING RISK IN MULTIPLE SCLEROSIS

RELATED APPLICATIONS

This application claims the benefit of U.S. Ser. No. 61/152,168, filed Feb. 12, 2009, the contents of which are incorporated by reference herein in their entirety.

FIELD OF THE INVENTION

The invention relates to methods and reagents for diagnosing and assessing the prognosis of multiple sclerosis.

BACKGROUND OF THE INVENTION

Multiple sclerosis (MS) is a chronic autoimmune inflammatory disease of the central nervous system (CNS). It is a common cause of persistent disability in young adults. In patients suffering from MS, the immune system destroys the myelin sheath of axons in the brain and the spinal chord, causing a variety of neurological pathologies. In the most common form of MS, Relapsing-Remitting (RRMS), episodes of acute worsening of neurological function (exacerbations, attacks) are followed by partial or complete recovery periods (remissions) that are free of disease progression. There is a clinical need for a simple serological assay that predicts: i) whether patients diagnosed as having RRMS have a high risk for rapid disease progression that results in high levels of inflammatory lesions in the CNS, as seen using magnetic resonance imaging (MRI), or in accumulation of clinical disabilities, and therefore might require aggressive disease modifying therapy (DMT); or ii) whether patients diagnosed as having RRMS will have a regular or relatively slow MS disease progression with less MRI activity and less accumulation of disabilities, thereby requiring less aggressive therapy.

SUMMARY OF THE INVENTION

The invention solves a long standing problem in the field of multiple sclerosis (MS)—how to predict the disease activity for MS patients having relapsing-remitting MS (RRMS). The method involves characterizing an individual as a member of one of two groups: (i) those who have a risk of rapid disease progression that results in high levels of inflammatory lesions in the CNS, as seen using magnetic resonance imaging (MRI), or in accumulation of clinical disabilities, and therefore might require aggressive disease modifying therapy (DMT); and ii) patients diagnosed as having RRMS that will have a regular or relatively slow MS disease progression with less MRI activity and less accumulation of disabilities, thereby requiring less aggressive therapy.

To enhance the ability of a physician to read and interpret an MRI scan, a contrast material, such as the chemical compound gadolinium, is often administered to highlight areas of inflammation in the brain. A gadolinium-enhanced MRI scan shows active lesions, meaning that there is a breakdown of the blood-brain barrier, and inflammation is present. Therefore, gadolinium-enhanced lesions are new—it is estimated that lesions will enhance with gadolinium for six weeks or fewer after lesion development. These lesions are defined as "contrast-enhancing lesions". In this manner, gadolinium allows the physician to determine which lesions are active and which lesions are inactive. This information is used to evaluate disease activity and determine if a relapse is occurring.

The present invention is based upon the discovery that IgM antibodies toward the antigen molecule Glc($\alpha$1,2)Gal($\beta$) (GAAB), which is found in the blood brain barrier (BBB), are found in higher levels in RRMS patients that have a contrast-enhancing T1 MRI lesion than in patients that do not have a contrast-enhancing T1 MRI lesion within the same time frame. Specifically, contrast-enhancing T1 MRI lesion frequency was found to correlate with more active RRMS disease. By "contrast-enhancing T1 MRI lesion" is meant a lesion that is visible via a T1 MRI scan after administration of a contrast agent to enhance the ability of a physician to read and interpret an MRI scan. For example, the contrast agent comprises gadolinium.

The invention provides methods of identifying a subject diagnosed with RRMS who will develop an active disease course demonstrated by MRI-detectable lesions. In one aspect, the MRI detectable lesions are contrast-enhancing T1 MRI lesions. First, a test sample is provided from a subject diagnosed RRMS. Suitable test samples include a biological fluid selected from the group consisting of whole blood, serum, and plasma. The level of an anti-Glc($\alpha$ 1,2)Gal($\beta$) antibody (GAAB) is detected/measured in the sample. Preferably, the antibodies are IgM type antibodies. The reference level in relation to the risk of having MRI-detectable lesions (e.g., contrast-enhancing T1 MRI lesions) in the CNS is a reference value from one or more MS patients that do not have any MRI-detectable lesions in the CNS. The levels of the antibodies in the test sample are compared to the levels of the antibodies in a control sample, wherein a higher level of the antibodies in the test sample compared to the level of the antibodies in a control sample indicates the subject is at risk of having an active disease as demonstrated by contrast-enhancing T1 MRI lesions in the central nervous system (CNS), and a rapid MS disease progression (active disease course) with a higher level of disabilities (breakthrough MS).

Alternatively, a low level of the antibodies in the test sample similar to the level of the antibodies in a control sample indicates the subject is unlikely to develop contrast-enhancing T1 MRI lesions, and will have a slow MS disease progression.

In some instances, MS patients have a poor prognosis despite treatment. The term "breakthrough disease" is used to indicate clinical or imaging evidence for disease activity or progression (e.g., measured by Expanded Disability Status Scale (EDSS score)) despite disease-modifying therapy (DMT). Breakthrough disease does not imply that the patient has not responded to treatment—it implies only that disease activity is present despite therapy. Prior to the invention, it was difficult to differentiate between a rapid progression good responder to DMT and a slow progressor with a poor response to DMT.

Accordingly, the invention provides methods of identifying a subject with RRMS who will develop breakthrough MS. First, a test sample is provided from a subject. Suitable test samples include a biological fluid selected from the group consisting of whole blood, serum, and plasma. An anti-Glc($\alpha$ 1,2)Gal($\beta$) antibody (GAAB) is detected/measured in the test sample. Preferably, the antibody is an IgM antibody. The levels of the antibodies in the test sample are compared to a reference level of the antibodies, wherein a higher level of the antibodies compared to the reference level of the antibodies correlates with breakthrough MS. A higher level of the antibodies compared to the reference level of the antibodies indicates that the prognosis of the subject is that the subject will develop contrast-enhancing T1 MRI-detectable lesions or breakthrough MS at a time in the future, i.e., subsequent to the detection of the antibodies. For example, the subject is identified as having a high likelihood of being diagnosed with MS as evidenced by MRI-detectable lesions even before an MRI analysis is carried out.

Alternatively, the levels of the antibody in the blood sample are compared to levels of the antibody in a reference sample and, a subject who will not progress to a breakthrough MS is differentiated by detection of an equal/similar or lower level of the antibody in the subject sample compared to levels of the antibody in the control sample.

The invention also provides a method of identifying a subject with RRMS who is likely to experience rapid progression of MS disease activity. First, a test sample is provided from a subject with RRMS. Suitable test samples include a biological fluid selected from the group consisting of whole blood, serum, and plasma. An anti-Glc ($\alpha$ 1,2) Gal ($\beta$) antibody (GAAB) is detected/measured in the test sample. Preferably, the antibodies are IgM type antibodies. The levels of the antibodies in the test sample are compared to the levels of the antibodies in a control sample, wherein a higher level of the antibodies in the test sample compared to the level of the antibodies in a control sample indicates the subject is at risk of having active MS disease progression.

Alternatively, a low level of the antibodies in the test sample equal, similar to, or lower than the level of the antibodies in a control sample indicates the subject is likely to have a slow MS disease progression within the same time period. The control in relation to the prediction of active MS disease progression is a reference value from one or more MS patients characterized as having contrast-enhancing T1 MRI lesions in the CNS.

The invention also provides a computer-readable medium having computer-executable instructions for performing a method. First, at least one first variable associated with the level of at least one antibody (e.g., Glc ($\alpha$ 1,2) Gal ($\beta$) antibody (GAAB)), in a blood sample of a patient is stored. Optionally, the antibody levels are detected via binding to immobilized glycans in a chamber or well, and emitting a fluorescent signal; chemiluminescence signal; or optical density signal by adding a pre-labeled secondary antibody recognizing a common reign in IgM isotype. Second, at least one second variable associated with at least one reference level is stored. The patient's risk factor for the relevant clinical question: i) RRMS patients who will develop an active disease course demonstrated by T1 MRI enhancing lesions; ii) RRMS patients who will develop breakthrough MS; or iii) RRMS patients who are likely to experience rapid progression of MS disease activity, is calculated as a function of at least the first and second variables. Finally, the risk factor is outputted. Optionally, the at least one first variable corresponds to levels of an anti-Glc ($\alpha$ 1,2) Gal ($\beta$) antibody in the sample.

By "reference level" is meant the mean, median, certain upper or lower percentile, or range level of an antibody in a defined cohort of MS individuals. For example, the cohort is characterized by RRMS patients that do not have any contrast-enhancing T1 MRI lesions in the CNS. An exemplary "reference level" of antibody is the mean plus 0.5, 1, 1.5, or 2 standard deviations (SD) of the mean, or the mean minus 0.5, 1, 1.5, or 2 SD of the mean. Preferably, the reference level is the mean antibody level plus 1.5 SD, or the mean minus 1.5 SD of the mean. The population of individuals is at least 5; at least 10, at least 25; at least 50; at least 100 or more individuals. Reference levels are obtained by measuring antibody levels (e.g., anti-Glc ($\alpha$ 1,2) Gal ($\beta$) antibody (GAAB)) in samples from a cohort of patients with a known MS progression profile, e.g., archived blood, serum, or plasma samples.

In practice, by examining a statistically-relevant cohort of patients (e.g., 50 patients, 100 patients, etc.) a reference sera sample similar to the chosen cutoff level is determined for the anti-Glc ($\alpha$ 1,2) Gal ($\beta$) antibody (GAAB), i.e., the upper 25%, the upper 20%, the upper 15%, the upper 10%; or the lower 25%, the lower 20%, the lower 15%, or the lower 10%. Antibody levels in the upper percentiles indicate a risk of having an active disease demonstrated by contrast-enhancing T1 MRI lesions in the central nervous system (CNS), and a rapid MS disease progression (active disease course), while antibody levels in the lower percentiles indicate a slow disease progression. Aliquots of the reference sera samples are prepared and kept frozen for future use. The reference sera samples are calibration samples, having a preset antibody level (cutoff level; reference level). When test samples are analyzed for their antibody levels, the test sample is examined in parallel with the reference/calibration/control sample. If the antibody level in the test sample is higher compared to the antibody level in the reference/calibration sample, the test sample is considered "positive", e.g., it belongs to the subgroup of RRMS patients with an elevated level of the antibody. Similarly, if the antibody level in the test sample is equal/similar or lower compared to the antibody level in the reference/calibration sample, the test sample is considered "negative", e.g., it belongs to the subgroup of RRMS patients without an elevated level of the antibody.

The clinical parameters of sensitivity, specificity, negative predictive value, positive predictive value and efficiency are calculated using true positives, false positives, false negatives and true negatives. A "true positive" sample is a sample positive for MS according to art-recognized methods for diagnosing/prognosing MS, which is also diagnosed positive according to a method of the invention. A "false positive" sample is a sample negative by an art-recognized method, which is diagnosed positive according to a method of the invention. Similarly, a "false negative" is a sample positive for an art-recognized analysis, which is diagnosed negative according to a method of the invention. A "true negative" is a sample negative for the assessed trait by an art-recognized method, and also negative according to a method of the invention. See, for example, Mousy (Ed.), Intuitive Biostatistics New York: Oxford University Press (1995), which is incorporated herein by reference.

As used herein, the term "sensitivity" means the probability that a laboratory method is positive in the presence of the measured trait. Sensitivity is calculated as the number of true positive results divided by the sum of the true positives and false negatives. Sensitivity essentially is a measure of how well a method correctly identifies those with the clinical question. In a method of the invention, the antibody values can be selected such that the sensitivity of diagnosing/prognosing an individual that will have a rapid MS progression is at least about 20%, and can be, for example, at least about 30%, 40%, 50%, 60%, 70%, 80% or 90%.

As used herein, the term "specificity" means the probability that a method is negative in the absence of the measured trait. Specificity is calculated as the number of true negative results divided by the sum of the true negatives and false positives. Specificity essentially is a measure of how well a method excludes those who do not have the measured trait. The antibody cut-off value can be selected such that, when the sensitivity is at least about 30%, the specificity of diagnosing/prognosing an individual is in the range of 60-70%, 80-85%, 90-95%, or 95-99.9%.

There are numerous advantages associated with measuring levels of anti-Glc($\alpha$1,2)Gal($\beta$) antibody (GAAB) to determine MS disease activity. First, although MRI scans are not typically painful, patients often find the experience of having an MRI scan, including the intravenous injection of contrast-enhancing agents, strange and anxiety-provoking. Using the methods described herein, patients merely need to provide a blood sample, rather than subject themselves to an MRI scan. Moreover, measuring blood levels of anti-Glc($\alpha$1,2)Gal($\beta$) antibody (GAAB) in patients with RRMS provides invaluable information upon which the treating physician relies to design the most effective treatment regimen. Anti-Glc ($\alpha$ 1,2) Gal ($\beta$) antibody levels also serve as a tool to convince RRMS patients to comply with treatment regimens prescribed by their physicians.

Other features and advantages of the invention will be apparent from the following description of the preferred embodiments thereof, and from the claims. Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, Genbank/NCBI accession numbers, and other references mentioned herein are incorporated by reference in their entirety. In the case of conflict, the present specification, including definitions, will control. In addition, the materials, methods, and examples are illustrative only and not intended to be limiting.

DETAILED DESCRIPTION

Multiple sclerosis (MS) is an inflammatory demyelinating disease of the central nervous system (CNS), though the exact etiology and pathogenesis have not yet been deciphered. Diagnosis of MS requires exclusion of diseases that could better explain the clinical, imaging, and paraclinical findings. The MS diagnosis criteria, also known as the revised McDonald criteria, define the parameters required for a subject having MS (Polman et al., 2005 Ann Neurol, 58: 840-6).

To better define suspected MS cases that may or may not meet the McDonald criteria, an International Panel of MS experts recently developed consensus-determined guidelines for differential diagnosis leading to MS (Miller et al., 2008 Multiple Sclerosis, 14:1157-1174). Magnetic resonance imaging (MRI) is a major tool utilized in diagnosing and monitoring MS disease activity, as this technology allows for the visualization of demyelinated regions in the brain.

Magnetic Resonance Imaging of MS Lesions

Magnetic resonance imaging (MRI), also known as nuclear magnetic resonance imaging (NMRI), is primarily a medical imaging technique used to visualize detailed internal structure and limited function of the human body. MRI provides much greater contrast between the different soft tissues of the body as compared to computed tomography (CT), making it especially useful in neurological (brain) imaging. Unlike CT, MRI does not use ionizing radiation, but uses a powerful magnetic field to align the nuclear magnetization of hydrogen atoms in water in the body. When the body is exposed to a strong magnetic field, the nuclei of the hydrogen atoms are directed into order, thereby acting as microscopic compass needles. Radio frequency (RF) fields are used to systematically alter the alignment of this magnetization, causing a change in the energy content of the hydrogen nuclei. Upon cessation of the pulse of radio waves, a resonance wave is emitted when the nuclei return to their previous state, thereby producing small differences in the oscillations of the nuclei, which are detectable by a computer scanner. The various types of MRI scans that are used (most commonly the T1-weighted scan and the T2-weighted scan) measure this relaxation time differently. Computer processing enables the production of a three-dimensional image that reflects the chemical structure of the imaged tissue, including differences in the water content and in movements of the water molecules. As water (composed of hydrogen and oxygen atoms) constitutes about two-thirds of the human body weight, this signal can be manipulated by additional magnetic fields to construct an image of the entire body, including the human brain.

MRI scans are particularly useful in the diagnosis and monitoring of MS, as these scans enable the visualization of demyelinated brain regions. Myelin is a dielectric (electrically insulating) material that forms a fatty layer (myelin sheath) around the axon of a neuron. Nerve cells communicate by propagating electrical signals (action potentials) down these long nerve axons insulated with myelin. During MS, the body's own immune system attacks and damages the myelin sheath. "Demyelination" refers to the loss of the protective myelin sheath surrounding nerve axons, and results in the disruption of nerve signals, thereby causing many symptoms associated with MS. As the layer of myelin that protects nerve fibers it composed of fat, the intact myelin sheath typically repels water. However, in demyelinated nerve fiber regions, the absence of the protective fat layer allows for the accumulation of water. Thus, as described above, the MRI scan detects the water in demyelinated regions, and such regions appear as either bright white spots or darkened areas, depending on the type of scan that is used. Regions in the brain or spinal column that have been demyelinated are called "lesions" or "plaques". Indeed, the phrase "multiple sclerosis" refers to scars (scleroses, i.e., plaques or lesions) in the white matter of the brain and spinal cord.

As described above, common MRI scan methods used for MS include the T1-weighted scan and the T2-weighted scan. In the brain, T1-weighted scans provide good gray matter/white matter contrast. A T1-weighted MRI scan shows "black holes" that display as dark areas on the MRI image. These so-called hypo-intense lesions are areas of permanent axonal damage. T1-weighted lesions can also be areas of edema (swelling), which are not permanent, and are not visible on subsequent scans. The T1-weighted scan is part of conventional MRI technology which is used to monitor and diagnose MS, usually in conjunction with a T2-weighted scan. The T2-weighted MRI scan shows the total number of lesions (lesion load) and disease burden. These are hyper-intense lesions, meaning that they appear as bright spots on the MRI image. The T2-weighted scan is part of conventional MRI technology, which is used to monitor and diagnose MS, usually in conjunction with a T1-weighted scan.

Sometimes it is not possible to generate enough image contrast to adequately show the anatomy or pathology of interest by adjusting the imaging parameters alone, in which case a contrast-enhancing agent may be administered. Contrast agents used in MRI for detection of MRI lesions are selected for their specific magnetic properties. The most commonly used intravenous contrast agents are based on chelates of gadolinium. When MS is suspected, the paramagnetic contrast material, gadolinium, is often administered to enhance the ability of a physician to read and interpret a T1 MRI scan. Contrast agents such as gadolinium are injected intravenously to enhance the appearance of blood vessels, tumors, or inflammation. Gadolinium-enhanced tissues and fluids appear extremely bright on T1-weighted images. To determine which lesions are enhanced with an administered contrast agent, a T1 scan is performed both before and after administration of the contrast agent (e.g., gadolinium). The use of contrast agents provides high sensitivity for detection of vascular tissues and permits assessment of brain tissue. The gadolinium-enhanced T1-weighted MRI scan supplies information about current disease activity by highlighting areas of breakdown in the blood-brain barrier, which correspond to areas of inflammation.

Gadolinium (Gd) is a rare element of the lanthanide series, with strong paramagnetic properties. Gadolinium administration markedly decreases the T1 relaxation time of adjacent mobile water protons. As a result, after IV gadolinium administration, there is a locally increased signal on T1-weighted images from CNS tissues where, normally, there is no blood brain barrier, e.g., the circumventricular organs, meninges, and choroid plexus, or where the barrier is abnormally compromised or even absent, as occurs in many types of lesions. This is the case of active MS lesions, in which enhancement correlates with altered blood brain barrier permeability in the setting of acute perivascular inflammation. Gadolinium reacts to areas of inflammation and will "light up" when a lesion is active, indicating demyelination is actively occurring. Therefore, gadolinium-enhanced lesions are relatively new, e.g., six weeks or fewer after lesion development. In this manner, administration of gadolinium before an MRI scan allows the physician to determine which lesions are active and which lesions are inactive. As described above, identification of active lesions via gadolinium-enhanced MRI scan also suggests that there is a breakdown of the blood-brain barrier. Lesions visible after administration of gadolinium are characterized as contrast-enhancing T1 MRI lesions.

In MS, the number of new contrast-enhancing lesions seen on monthly MRI scans is the most widely used response variable in MRI-monitored studies of experimental treatments (Sormani et al., 1999 J Neurological Sci, 163(1): 74-80). This information is used to evaluate disease activity and determine if a relapse is occurring. For example, the presence of gadolinium-enhancing lesions while on interferon beta therapy suggests a future clinical and MRI disease worsening (Rudick, et al. 2004 Ann Neurol, 56: 548-55; Rio, et al. 2008 Mult Scler, 14: 479-84; and Durelli, et al. 2008 J Neurol Neurosurg Psychiatry, 79: 646-51.)

Prognostic Value of Anti-Glc($\alpha$ 1,2)Gal($\beta$) Antibody (GAAB) Levels

As described below, high levels of anti-Glc($\alpha$ 1,2)Gal($\beta$) antibody (GAAB) compared to the reference level of the antibody identify Relapsing-Remitting MS (RRMS) patients who will develop an active disease course demonstrated by contrast-enhancing T1 MRI lesions. Moreover, high levels of anti-Glc($\alpha$1,2)Gal($\beta$) antibody (GAAB) compared to the reference level of the antibody identify RRMS patients who will develop breakthrough MS, i.e., MS disease activity despite therapy.

The course of MS disease follows unpredictable patterns of evolution and widely variable timetables, with disability accumulation adhering to no particular blueprint making it difficult or impossible to accurately determine the prognosis of individual patients (Vollmer T, 2007 J Neurol Sci, 256 Suppl 1:S5-13). Heterogeneity can be related to the timeframe a clinically isolated syndrome (CIS) patient will have the next relapse or the response to disease modifying therapy (DMT). Heterogeneity can also refer to the disease progression rate and accumulation of disabilities. Heterogeneity can also refer to the appearance or non-appearance of contrast-enhancing T1 MRI lesions in the CNS. In many instances, MS patients have a poor prognosis despite treatment. Specifically, the term "breakthrough disease" is used to indicate clinical or Magnetic Resonance Imaging (MRI) evidence for disease activity or progression (as may be measured by Expanded Disability Status Scale (EDSS score)) despite DMT (Rudick and Polman 2009, Lancet Neurology, 8:545-559). Breakthrough disease does not imply that the patient has not responded to treatment—it implies only that disease activity is present despite therapy.

The invention describes methods regarding the prediction of RRMS patients who will develop an active disease course demonstrated by contrast-enhancing T1 MRI lesions. The method involves characterizing an individual as a member of one of two groups: (i) those who have a risk of rapid disease progression that results in high levels of inflammatory lesions in the CNS, as seen using magnetic resonance imaging (MRI), or in accumulation of clinical disabilities, and therefore might require aggressive disease modifying therapy (DMT); and ii) those patients diagnosed as having RRMS that will have a regular or relatively slow MS disease progression with less MRI activity and less accumulation of disabilities, thereby requiring less aggressive therapy.

The earliest clinical presentation of RRMS is the CIS. The current clinical practice is to treat CIS patients suggestive of MS and newly diagnosed patients with first line DMT. Physicians point out the benefits of starting treatment early, but not all patients comply. A recent survey among United States neurologists revealed that at least 10% of newly diagnosed MS patients delayed their treatment due to their fear of injections (Perrin et al., 2009 JMCP, 15(7): 572). Therefore, the segregation of patients at an early stage of disease based on the risk to rapid progression of MS disease and inflammatory lesions can be an important convincing tool for patient compliance with early DMT treatment, because those in group (i) will agree to receive DMT, whereas those in group (ii) can delay treatment until the next clinical or image episode.

Another aspect of current clinical practice is switching to another existing DMT due to the failure of the first DMT. Switching can be for another $1^{st}$ line DMT or to a more aggressive $2^{nd}$ line ($2^{nd}$ generation) DMT. Therefore, the segregation of RRMS patients based on predicting the risk of rapid progression of MS and the risk of having inflammatory lesions (e.g., contrast-enhancing T1 MRI lesions that are indicative of an active inflammation in the CNS) is a critical factor in the determination of a treatment regimen, because those in group (i) will receive an aggressive DMT regimen, whereas those in group (ii) receive less aggressive DMT or another $1^{st}$ line DMT.

During symptomatic attacks, administration of high doses of intravenous corticosteroids, such as methylprednisolone is the routine therapy for acute relapses. The aim of this kind of treatment is to end the attack sooner and leave fewer lasting deficits in the patient. Although generally effective in the short term for relieving symptoms, corticosteroid treatments do not appear to have a significant impact on long-term recovery (Brusaferri and Candelise, 2000 J. Neurol., 247(6): 435-42). Potential side effects include osteoporosis and impaired memory, the latter being reversible (Dovio et al., 2004 Clin. Endocrinol. Metab., 89(10): 4923-8; Uttner et al., 2005 Neurology, 64(11): 1971-3). Severe attacks which do not respond to corticosteroids might be treated by plasmapheresis. The earliest clinical presentation of relapsing-remitting MS (RRMS) is the clinically isolated syndrome (CIS). Several studies have shown that treatment with interferons during an initial attack can decrease the chance that a patient will develop clinical MS (Jacobs et al., 2000 N Engl J Med, 343(13): 898-904; Comi et al., 2001 Lancet, 357(9268): 1576-82; Kappos et al., 2007 Lancet, 370(9585): 389-97). These and other CIS studies that showed the benefit in early treatment with DMT evolved to current clinical practice in which newly diagnosed RRMS and CIS suggestive of MS patients are initiating DMT treatment immediately after first presentation and abnormal MRI scan.

Six disease-modifying treatments have been approved by regulatory agencies of different countries for RRMS (Rudick and Polman 2009, Lancet Neurol, 8: 545-559). Three are interferons: two formulations of interferon beta-1a (trade names Avonex®, CinnoVex™, ReciGen and Rebif®) and one of interferon beta-1b (U.S. trade name Betaseron®, in Europe and Japan Betaferon®). A fourth medication is glatiramer acetate (Copaxone®). The fifth medication, mitoxantrone, is an immunosuppressant also used in cancer chemotherapy, approved only in the USA and largely for secondary progressive MS. The sixth is natalizumab (marketed as Tysabri®). All six medications are modestly effective at decreasing the number of attacks and slowing progression to disability, although their efficacy rates differ, and studies of their long-term effects are still lacking (Ruggieri et al., 2007 CNS Drug Rev, 13(2): 178-91; Munari et al., *Cochrane Database of Systematic Reviews* 2003, Issue 4. Art. No.: CD004678; Rice et al., 2001 *Cochrane Database Syst Rev* (4): CD002002; Martinelli Boneschi et al., 2005 *Cochrane Database Syst Rev* (4): CD002127). Comparisons between immunomodulators (all but mitoxantrone) show that the most effective is natalizumab, both in terms of relapse rate reduction and halting disability progression (Johnson K P, 2007 J. Neurol. Sci., 256 Suppl 1: S23-8); it has also been shown to reduce the severity of MS. Mitoxantrone may be the most effective of them all (Gonsette R E, 2007 Expert opinion on pharmacotherapy, 8(8): 1103-16); however, it is generally not considered as a long-term therapy, as its use is limited by severe cardiotoxicity (Murray T J, 2006 Expert opinion on drug safety, 5 (2): 265-74). The interferons and glatiramer acetate are delivered by frequent injections, varying from once-per-day for glatiramer acetate to once-per-week (but intra-muscular) for Avonex®. Natalizumab and mitoxantrone are given by IV infusion at monthly intervals. These DMTs are also known as $1^{st}$ line DMT.

Recently, a "true" $2^{nd}$ generation DMT successfully completed phase III clinical trials. Fingolimod (FTY720) and Mylinax (Cladrabine) have shown higher efficacy as compared to the $1^{st}$ line DMT studies in the active arm during these phase III clinical trials. 2nd generation Disease Modifying Therapy (DMT) is currently being introduced to the MS market; however, adverse side affects such as death from Herpes infections and skin cancers were reported during the phase III clinical studies. Due to the severe side effects of the $2^{nd}$ generation DMTs, they will not be prescribed to all patients. In addition, four other agents with more active efficacy than $1^{st}$ line DMTs, but with adverse side effects, are currently in phase III clinical trials.

The heterogeneity of disability progression in MS patients is seen by observing the Expanded Disability Status Scale (EDSS) in populations having an RRMS onset at different time intervals. After 5 years from disease onset, 10-15% of RRMS patients reached an expanded disability status score (EDSS) of 3.0 (corresponding to a patient who is fully ambulatory, but has moderate disability), after 8-12 years, 27%-30% of RRMS patients had an EDSS score of 3, and by 20 years, 39% of RRMS patients had an EDSS score of up to 3, while 39% of RRMS patients had an EDSS score of at least 6 (corresponding to a patient needing assistance of a cane to walk; Simone I L et al., 2002 Neurology, 24;59(12): 1922-8; Pittock S J et al., 2004 Ann Neurol, 56: 303-306; Tintoré M et al., 2006 Neurology, 67: 968-972).

Recently, clinically isolated syndrome (CIS) was "re-defined" as a monophasic presentation with suspected underlying inflammatory demyelinating disease (Miller D H et al., 2008 Multiple Sclerosis, 14: 1157-1174). "Monophasic presentation" implies a single clinical episode at first presentation that is of relatively rapid onset. Multiple simultaneous clinical/paraclinical presentations (representing dissemination in space) are possible, although dissemination in time should not be evident. Four classes of CIS were defined based on whether the monophasic clinical presentation has mono- or multifocal clinical or MRI features (Miller D H et al., 2008 Multiple Sclerosis, 14:1157-1174). Finally, there should be reasonable grounds for suspecting inflammatory demyelinating disease as the underlying pathology.

In CIS patients suggestive of multiple sclerosis, the EDSS progression is as follows. Twenty-five percent (25%) of CIS patients have an EDSS score of at least 6.0 after 20 years. Approximately 45% of CIS patients reach an EDSS score of 3.0 during the same 20 year period, while the remaining 30% of CIS patients have an EDSS score under 3.0 after 20 years (Fisniku L K et al., 2008 Brain, 131: 808-817). Thus, a certain subpopulation of patients with RRMS onset have a more severe/active disease, in that these patients have a higher probability of developing a greater disability level, i.e., rapid or "fast" MS patients. Certain clinical (e.g., male gender, late age of onset, and polysymptomatic onset) and paraclinical factors (e.g., number, volume, and site of magnetic resonance Imaging (MRI) lesions, and presence of oligoclonal bands (OBs) in cerebrospinal fluid (CSF)) have shown a moderate ability to predict patients whose disability will progress more rapidly (Tintoré M et al., 2006 Neurology, 67:968-972; and Bergamaschi R 2007 Int Rev Neurobiol, 79:423-447). However, these predictive variables have limitations and only seem to aid in disability prediction of up to an EDSS score of 4 (Confavreux C et al., 2003 Brain, 126:770-782). As all current Disease Modifying Therapy (DMT) can only be utilized in patients with an EDSS score lower than 6.5, and as $2^{nd}$ generation aggressive DMT are associated with adverse side affect or are recently completed phase III studies, a set of prognostic tools that can improve the ability of the clinician to predict when a CIS patient will have a next relapse or if a CIS patient will progress quickly is needed. Such a prognostic tools will aid in the appropriate counsel of patients, identification of patients for more aggressive DMT, and improve the design and analysis of therapeutic trials (Miller D H, 2004 NeuroRx, 1:284-294; Bergamaschi R 2007 Int Rev Neurobiol, 79:423-447).

Prior to the invention, no known antigenic specificity profile existed to aid in the determination of disease activity (existence of an active MRI lesion), or disease severity (breakthrough disease). A test such as the one described herein that provides information regarding existence of active MRI lesions or how fast MS is likely to progress informs a physician to appropriately tailor therapeutic intervention. The search has been ongoing for useful serum derived biomarkers, including antibodies. Serum IgM antibodies to an N-glucosylated peptide were specifically increased in relapsing remitting multiple sclerosis (RRMS) patients (Lolli F, et al. 2005 *Proc Natl Acad Sci USA*, 102: 10273-78; Lolli F, et al. 2005 *J Neuroimmunol*, 167: 131-37). High antibody titers to two myelin peptides, myelin oligodendrocyte glycoprotein (MOG) and myelin basic protein (MBP) were reported by some (Berger T, et al. 2003 *N Engl J Med*, 349: 139-45), but not others (Kuhle J, et al. 2007 *N Engl J Med*, 356: 371-78) to predict early relapse in CIS patients. The finding of IgG antibody formation specifically in the cerebrospinal fluid (CSF), but not in a corresponding serum (i.e., oligoclonal banding), has been a useful test for diagnosis and differential diagnosis of MS (Freedman M S, et al. 2005 *Arch Neurol*, 62:865-70).

Prior to the invention, there was no specific serum-based biomarker known to be indicative of MS disease activity as measured by the presence of contrast-enhancing T1 MRI lesions in the CNS. As described below, antibody levels (e.g., anti-Glc ($\alpha$ 1,2) Gal ($\beta$) antibody (GAAB)) were measured by enzyme immunoassay in a cohort of RRMS (n=148) patients. All patients had undergone an MRI scan; 51 patients were found to have contrast-enhancing T1 MRI lesions, and 97 did not have contrast-enhancing T1 MRI lesions. The levels of anti-Glc ($\alpha$ 1,2) Gal ($\beta$) IgM antibody (GAAB) were significantly higher in patients with contrast-enhancing T1 MRI lesions as compared to patients without contrast-enhancing T1 MRI lesions. Based on Receiver Operating Characteristics (ROC) analysis, a cutoff level and reference level were defined. Based on multi-variance logistic regression models, anti-GAAB IgM levels above cutoff were found to be independent predictors of MRI activity (p=0.003, OR 3.07, CI95 1.44-6.55).

Example 1

Anti-Glc($\alpha$1,2)Gal($\beta$) (GAAB) IgM Antibodies Differentiate Between RRMS Patients with and without Contrast-Enhancing T1 MRI CNS Lesions The study was performed on sera that were collected from patients who participated in the accelerated cure project (ACP at MA, USA). Sera was donated to the ACP bio-repository, which also keeps the related clinical records in a database. Analysis was performed on thawed serum samples that were retrospectively collected and stored frozen (−80° C.). Patients included in the analysis were RRMS patients that were previously tested by contrast-enhancing T1-weighted spin-echo magnetic resonance imaging (MRI) within 6 years of serum collection. The cohort included relapsing remitting multiple sclerosis (RRMS) patients (n=148, mean age, 38.4±7.5, 116 female). Time from diagnosis was 4.7 years, 95% CI 3.9-5.5 years. Patients' serum samples were screened for levels of anti-GAAB IgM using enzyme immune assay.

Enzyme Immuno-Assay for Anti-GAAB IgM

Each sample was tested for levels of anti-GAAB IgM antibodies using the enzyme immuno-assay (EIA) method in a 96 micro-well plate platform. A P-Nitrophenyl derivative of Glc($\alpha$ 1,2)Gal($\beta$) was bound to well walls as previously described (Schwarz, et al., 2003 *Glycobiology*, 13(11): 749-754). Sera measurements were done in duplicate, each plate included a 5 points calibration curve. Results were reported in arbitrary EIA Units (EU).

EIA Procedures

The serum samples were stored frozen and were transported frozen to Glycominds Ltd., Lod, Israel. Samples were stored in −80° C. until use. Prior to use, the samples were thawed by incubation in 37° C. for 2 hours. IgG depletion was performed using a commercial anti-rheumatoid factor removal reagent (RFRR; Chemichon, Temacula, Calif., USA). Serum samples were diluted 1:1200 in a sample diluent, dispensed into the wells in duplicates, and incubated for 180 min at 4° C., then washed with wash buffer. Bound antibodies were labeled with horseradish peroxidase (HRP)-conjugated goat anti-human IgM type-specific antibody, washed, and 3,3',5,5'-tetramethylbenzidine was added for detection. After 30 minutes, the enzymatic reaction was stopped with 1% sulfuric acid solution and optical density (OD) in the wells was read at 450 nm with a microwell plate reader (Wallac, Turku, Finland). Each plate included a 5 point calibration curve with a preset unit value for each point on the curve. The calibration curve used to calculate the EIA units (EU), and to normalize results obtained from different plates. Results were reported in EU.

Statistical Analysis

Statistical analyses were performed using MedCalc for Windows, version 11.1.5.0 (MedCalc Software, Mariakerke, Belgium). Descriptive statistics are presented to describe characteristics of the study populations. Numerical variables were compared across groups by a Student's T Test. Multi-variable logistic regression models were constructed to assess antibody associations while adjusting for the confounders age and gender, odds ratio (OR) was reported for binomial variables. For rates comparisons between groups the Fisher's exact test was performed. P values <0.05 were considered significant. Receiver operator characteristics (ROC) curve analysis was used for choosing optimal cutoff level. Cutoff level was determined based on the anti-GAAB IgM levels in group of RRMS patients that do not have T1 contrast-enhancing MRI lesions findings, and was set to the upper 18 percentile of this group.

Figure 1:
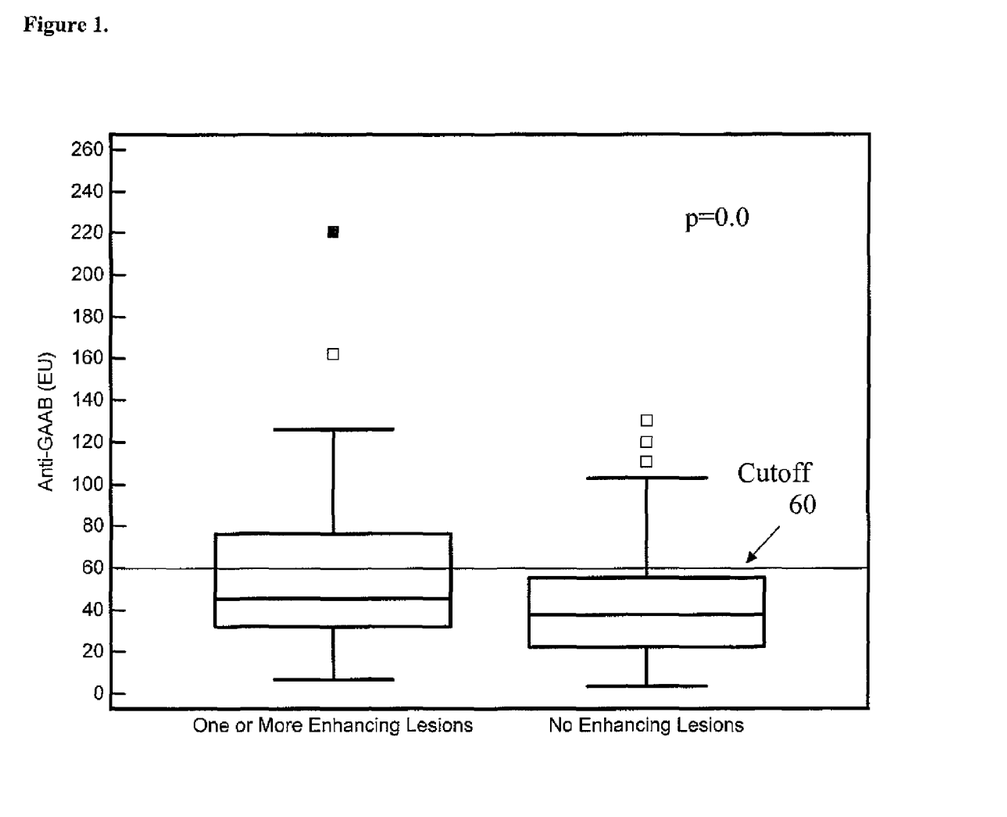
FIG. 1 shows box plots of anti-Glc ($\alpha$ 1,2) Gal ($\beta$) IgM antibody (GAAB) levels in patients with and without contrast-enhancing MRI lesions. Median values, 25%/75% quartiles, and outliers are presented. Empty squares are outliers defined as larger than the upper quartile plus 1.5 times the interquartile range. Shaded squares are far outliers defined as larger than the upper quartile plus 3 times the interquartile range. Anti-GAAB levels in patients without contrast-enhancing MRI lesions and in patients with contrast-enhancing MRI lesions were significantly different (p=0.04, T-Test).

The antibody EU levels of anti-GAAB were compared between patients that had one or more enhancing lesions and patients that had no enhancing lesions. Patients having one or more enhancing lesions had significantly higher levels of anti-GAAB than patients with no enhancing lesions (Table 1 and FIG. 1).

TABLE 1

Anti-GAAB levels are significantly higher in patients with one or more T1 contrast-enhancing MRI lesions as compared to patients without T1 contrast-enhancing lesions

| Biomarker | One or More Enhancing Lesions (n = 51) | | No Enhancing Lesions (n = 97) | | P-Value* |
|---|---|---|---|---|---|
| | Median | 95% CI | Median | 95% CI | |
| Anti-GAAB (EU) | 45.7 | 36.4-66.1 | 37.8 | 34.5-43.0 | 0.04 |

*Welch test, because of unequal variances.

Table 2 shows a logistic regression model testing the ability of the variables (e.g., anti-GAAB (EU), age, gender, and time from blood draw to MRI) to differentiate RRMS patients that are more likely to have an enhancing lesion from RRMS patients that are less likely to have an enhancing legion. Anti-GAAB (by EU values) is the only independent variable associated with the presence of contrast enhancing T1 MRI lesions.

TABLE 2

Overall Model Fit

| | |
|---|---|
| Null model −2 Log Likelihood | 190.635 |
| Full model −2 Log Likelihood | 1183.782 |
| Chi-square | 6.853 |
| DF | 1 |
| Significance level | P = 0.0088 |

Coefficients and Standard Errors

| Variable | Coefficient | Std. Error |
|---|---|---|
| Anti-GAAB | 0.01406 | 0.005626 |
| Constant | −1.3383 | P = 0.0124 |

TABLE 2-continued

Variables that were taken out of the model

Age
Sex

Figure 2:
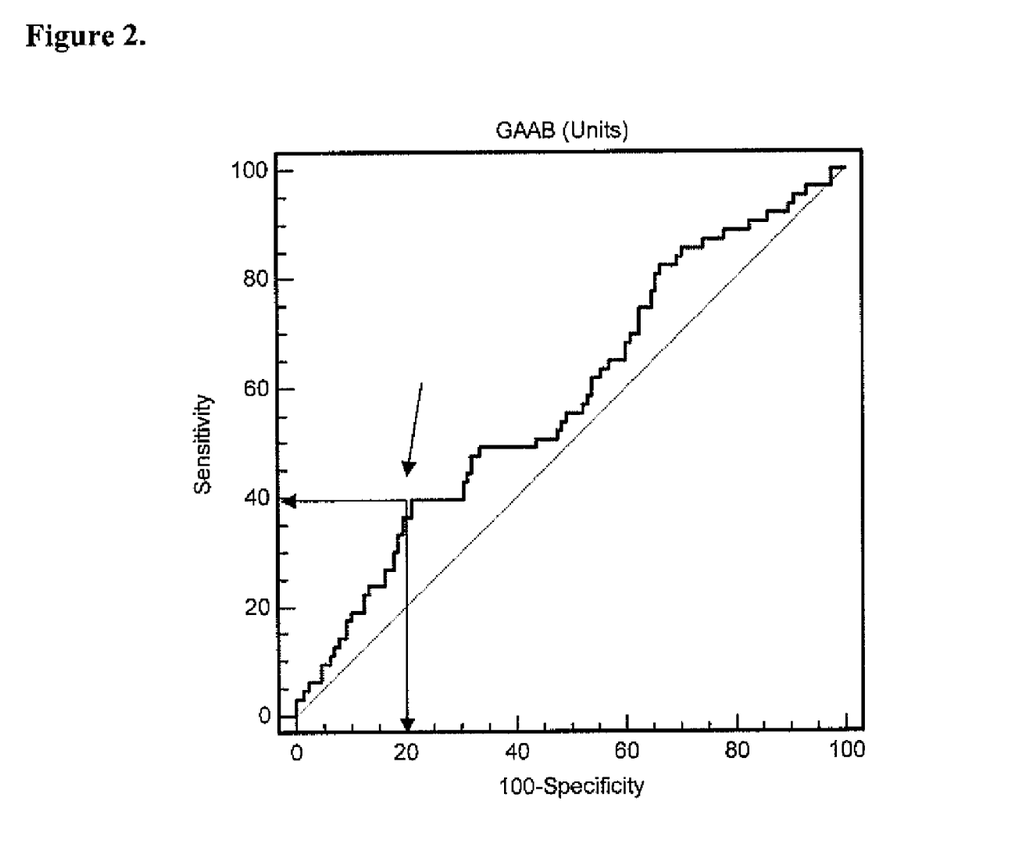
FIG. 2 shows a Receiver Operating Characteristics (ROC) curve for different anti-Glc ($\alpha$ 1,2) Gal ($\beta$) IgM antibody (GAAB) cutoff values (EU) for differentiating between RRMS patients (n=51) that have a contrast-enhancing lesion and those that do not (n=97). The area under the curve (AUC) was 0.603 (p=0.02). ROC curve analysis enabled a determination of the optimal cutoff point as the upper $20^{th}$ percentile of the group of patients that do not have contrast-enhancing T1 MRI lesions. The arrow indicates the sensitivity and specificity at the chosen cutoff level.

In order to determine the anti-GAAB EU cutoff level for detecting patients that are more likely to have an enhancing lesion, an ROC curve analysis was performed (FIG. 2 and Table 3). Table 3 demonstrates the diagnostic performance of the assay over a range of possible cutoff values. Each line represents a cutoff value based on anti-GAAB IgM levels of a certain patient. The sensitivity, specificity, LR(+), LR(−), and number of true positive, true negative, false positive, and false negative patients is presented in Table 3 for each possible cutoff. The cutoff was chosen as the upper $18^{th}$ percentile of the group of patients without enhancing lesions, e.g., 60EU (59.61 EU in Table 3). Sera from patient No. 17908, was chosen as the reference sample that represents the cutoff value. All other tested samples were compared to this sample.

Samples that have higher levels of anti-GAAB then the reference levels of sample No 17908 were considered as positive. These patients have a high risk for developing enhancing MRI lesions and breakthrough MS. At this cutoff level, the sensitivity is 41%, specificity 82%, and the positive likelihood ratio (LR+) is 2.22, i.e., the probability of a patient being positive (above cutoff) for the anti-GAAB test and developing at least one enhanced T1 lesion is increased by more than two. The negative likelihood ratio (LR−) is 0.72, i.e., the probability of a patient being negative for the anti-GAAB test and developing at least one enhanced T1 lesion is decreased by 28%.

Table 3 shows the ability of anti-GAAB to differentiate between RRMS patients that are more likely to have an enhancing lesion and RRMS patients that are less likely to have an enhancing lesion, for a set of cutoff values. The cutoff values are based on anti-GAAB IgM levels of the patients. The sensitivity, specificity, LR(+), LR(−), and number of true positive, true negatives, false positive, and false negative patients is presented for each possible cutoff.

TABLE 3

| Patient ID | GAAB (Units) (Positive test > cutoff) | Sensitivity | 95% CI | Specificity | 95% CI | LR (+) | LR (−) | True positive | True negative | False positive | False negative |
|---|---|---|---|---|---|---|---|---|---|---|---|
| 16940 | 57.24 | 0.45 | 0.311 to 0.597 | 0.804 | 0.711 to 0.878 | 2.30 | 0.68 | 23 | 78 | 19 | 28 |
| 17128 | 59.02 | 0.45 | 0.311 to 0.597 | 0.814 | 0.723 to 0.886 | 2.43 | 0.67 | 23 | 79 | 18 | 28 |
| 17063 | 59.10 | 0.43 | 0.293 to 0.578 | 0.814 | 0.723 to 0.886 | 2.32 | 0.70 | 22 | 79 | 18 | 29 |
| 17908 | 59.61 | 0.41 | 0.276 to 0.558 | 0.814 | 0.723 to 0.886 | 2.22 | 0.72 | 21 | 79 | 18 | 30 |
| 16932 | 63.56 | 0.39 | 0.258 to 0.539 | 0.814 | 0.723 to 0.886 | 2.11 | 0.75 | 20 | 79 | 18 | 31 |
| 17357 | 64.39 | 0.39 | 0.258 to 0.539 | 0.825 | 0.734 to 0.894 | 2.24 | 0.74 | 20 | 80 | 17 | 31 |
| 16922 | 65.95 | 0.37 | 0.241 to 0.519 | 0.825 | 0.734 to 0.894 | 2.13 | 0.76 | 19 | 80 | 17 | 32 |
| 17058 | 66.13 | 0.35 | 0.224 to 0.499 | 0.825 | 0.734 to 0.894 | 2.01 | 0.78 | 18 | 80 | 17 | 33 |
| 17861 | 66.32 | 0.35 | 0.224 to 0.499 | 0.835 | 0.746 to 0.903 | 2.14 | 0.77 | 18 | 81 | 16 | 33 |
| 17900 | 67.31 | 0.33 | 0.208 to 0.479 | 0.835 | 0.746 to 0.903 | 2.02 | 0.80 | 17 | 81 | 16 | 34 |
| 17346 | 67.71 | 0.31 | 0.191 to 0.459 | 0.835 | 0.746 to 0.903 | 1.90 | 0.82 | 16 | 81 | 16 | 35 |
| 17910 | 68.15 | 0.29 | 0.175 to 0.438 | 0.835 | 0.746 to 0.903 | 1.78 | 0.85 | 15 | 81 | 16 | 36 |
| 17025 | 68.88 | 0.27 | 0.159 to 0.417 | 0.835 | 0.746 to 0.903 | 1.66 | 0.87 | 14 | 81 | 16 | 37 |
| 17138 | 70.69 | 0.27 | 0.159 to 0.417 | 0.845 | 0.758 to 0.911 | 1.78 | 0.86 | 14 | 82 | 15 | 37 |
| 16931 | 72.35 | 0.27 | 0.159 to 0.417 | 0.856 | 0.770 to 0.919 | 1.90 | 0.85 | 14 | 83 | 14 | 37 |

TABLE 3-continued

| Patient ID | GAAB (Units) (Positive test > cutoff) | Sensitivity | 95% CI | Specificity | 95% CI | LR (+) | LR (−) | True positive | True negative | False positive | False negative |
|---|---|---|---|---|---|---|---|---|---|---|---|
| 17470 | 73.98 | 0.27 | 0.159 to 0.417 | 0.866 | 0.782 to 0.927 | 2.05 | 0.84 | 14 | 84 | 13 | 37 |
| 17067 | 75.22 | 0.27 | 0.159 to 0.417 | 0.876 | 0.794 to 0.934 | 2.22 | 0.83 | 14 | 85 | 12 | 37 |
| 17188 | 75.85 | 0.25 | 0.143 to 0.396 | 0.876 | 0.794 to 0.934 | 2.06 | 0.85 | 13 | 85 | 12 | 38 |

Logistic regression (Table 4) analysis including all variables (i.e., anti-GAAB positive/negative (positive >60 EU, negative <60 EU), age, sex and time from blood draw to MRI) demonstrated that the only predictive variable in the model was anti-GAAB (positive >60 EU/negative <60EU). Anti-GAAB is the only independent variable associated with the presence of enhancing T1 MRI lesions. The odds ratio of patients having levels above cutoff to have one or more enhancing lesions is 3.07 (CI 95% 1.44 to 6.55).

TABLE 4

Overall Model Fit

| Null model −2 Log Likelihood | 190.635 |
| Full model −2 Log Likelihood | 182.104 |
| Chi-square | 8.531 |
| DF | 1 |
| Significance level | P = 0.0035 |

Coefficients and Standard Errors

| Variable | Coefficient | Std. Error |
|---|---|---|
| Anti-GAAB (positive cutoff ≧60) | 1.1224 | 0.3862 |
| Constant | −0.9683 | P = 0.0037 |

Variables that were taken out of model

Age (years)
Time from BC to Brain MRI (months)
Sex

Odds Ratios and 95% Confidence Intervals

| Variable | Odds Ratio | 95% CI |
|---|---|---|
| Anti-GAAB (positive cutoff ≧60) | 3.07 | 1.44 to 6.55 |

The results presented herein demonstrate that anti-GAAB IgM differentiates between RRMS patients having a more active and severe disease as measured by contrast enhancing T1 MRI lesions. The levels of anti-GAAB IgM in the blood of RRMS patients that are higher than cutoff value that was determined based on anti-GAAB levels in a population of RRMS patients that did not have contrast-enhancing lesions T1 MRI lesions.

Figure 3:
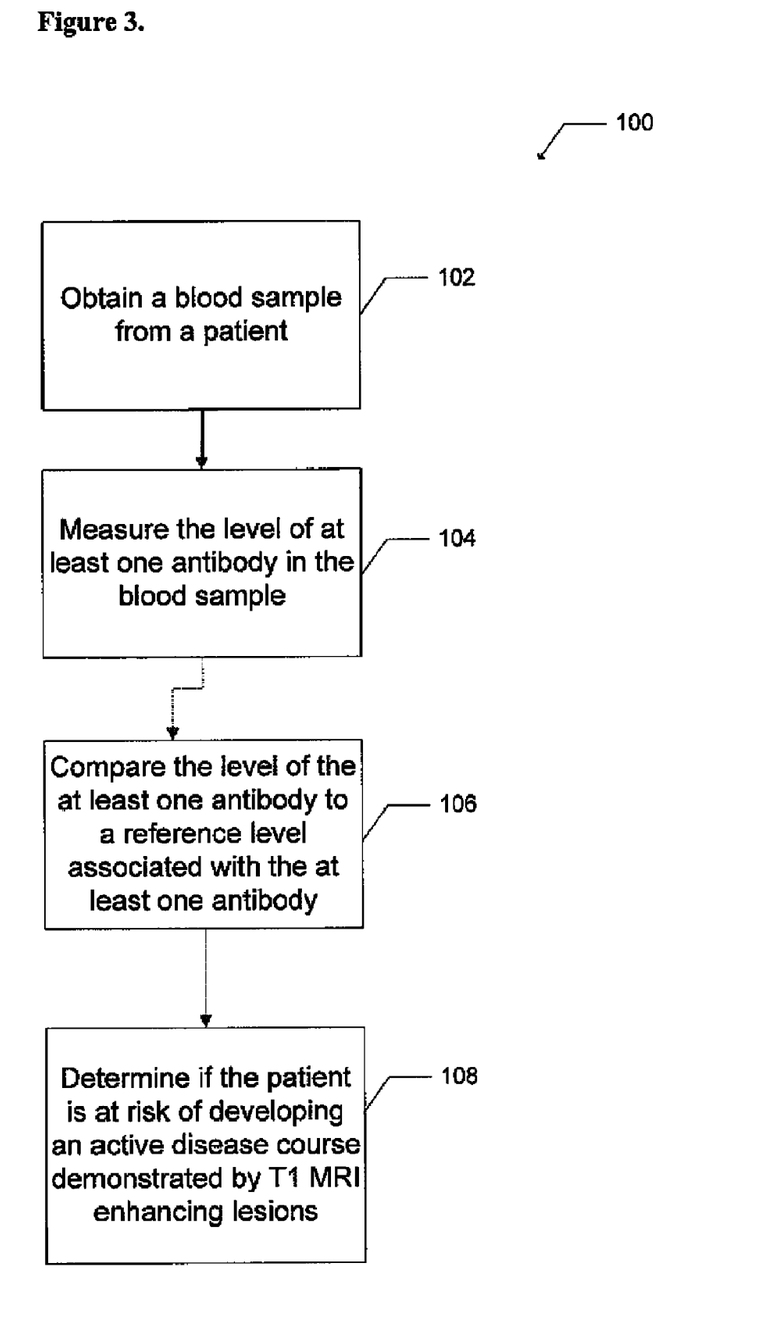
FIG. 3 shows a block flow diagram of a process of determining whether a patient is likely to develop an active disease course demonstrated by contrast-enhancing T1 MRI lesions.

In one aspect, referring to FIG. 3, a process (100) for determining if an RRMS patient is at risk of developing an active disease course demonstrated by T1 MRI enhancing lesions includes the stages shown. In the process (100), a level of at least one antibody in a patient sample, e.g., blood, is compared to a reference level. The process (100), however, is exemplary only and not limiting. The process (100) may be altered, e.g., by having stages added, removed, or rearranged. In an embodiment, the process (100) is implemented on a system including one or more computers or computer networks configured to read and execute computer-readable instructions stored on computer-readable mediums. A computer-readable medium is defined as any kind of computer memory such as floppy disks, conventional hard disks, CD and DVD ROMS, Flash ROMS, nonvolatile ROM, and RAM. The computers can be configured to receive data from a user via a user interface, or automatically via machine interface (e.g., a USB connection to a blood analyzer).

At stage 102, a test sample (e.g., whole blood, serum, or plasma) is obtained from a patient. Optionally, the patient's blood sample is collected by venipuncture. Following blood collection, the blood will clot, and the serum is separated from the blood clot by centrifugation of the collection tube. Sera samples are collected from a patient and stored prior to use, e.g., the sample is stored at −20° C., −70° C. or −80° C. until use. At stage 104, the level of at least one antibody is measured. For example, in an embodiment, levels of an anti-Glc (α 1, 2) Gal (β) (GAAB) antibody are detected. Optionally, levels of an anti-Glc (α 1, 2) Gal (β) (GAAB) IgM isotype antibody are detected.

At stage 106, the level of at least one antibody in the test sample is compared to one or more reference levels. Optionally, a computer or computer network is used to make the comparison. For example, the reference levels are stored on a computer-readable medium associated with computer or computer network, and the patient's at least one antibody level is received via an input device (e.g., keyboard, GUI, COM port).

At stage 108, the patient's risk factor for developing an active disease course demonstrated by T1 MRI enhancing lesions is determined. In an embodiment, a computer can be used to generate an output (e.g., report, message, display) to indicate the corresponding risk factor.

Figure 4:
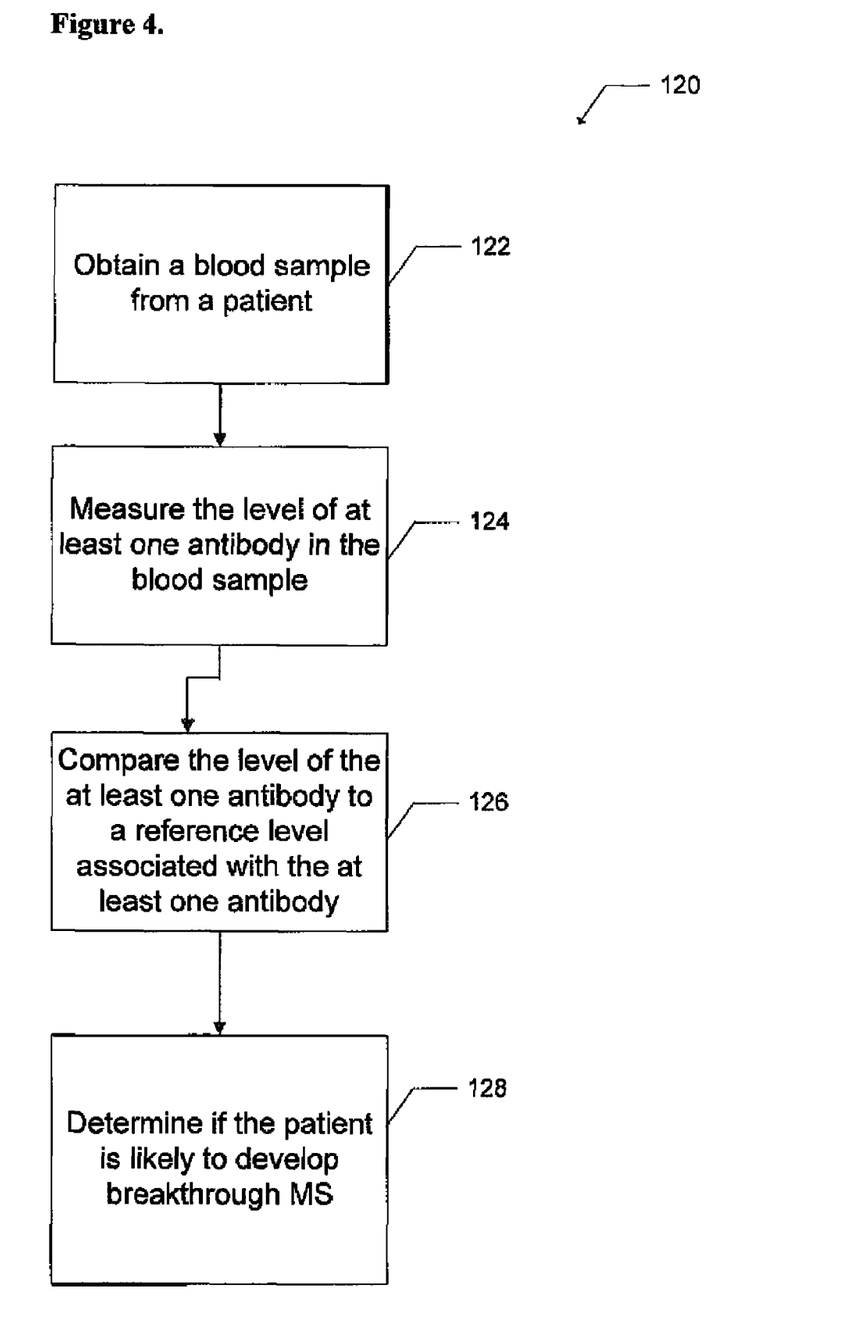
FIG. 4 shows a block flow diagram of a process of determining whether a patient is likely to develop breakthrough MS.

In another aspect, referring to FIG. 4, a process (120) for determining if a patient is likely to develop breakthrough MS includes the stages shown. In the process (120), a level of at least one antibody in the patient sample, e.g., blood, is compared to a reference level. The process (120), however, is exemplary only and not limiting. The process (120) may be altered, e.g., by having stages added, removed, or rearranged. In an embodiment, the process (120) is implemented on a system including one or more computers or computer networks configured to read and execute computer-readable instructions stored on computer-readable mediums. A computer-readable medium is defined as any kind of computer memory such as floppy disks, conventional hard disks, CD and DVD ROMS, Flash ROMS, nonvolatile ROM, and RAM. The computers can be configured to receive data from a user via a user interface, or automatically via machine interface (e.g., a USB connection to a blood analyzer).

At stage 122, a test sample (e.g., whole blood, serum, or plasma) is obtained from a patient. At stage 124, the level of at least one antibody is measured. For example, in an embodiment, levels of an anti-Glc (α 1, 2) Gal (β) (GAAB) antibody are detected. Optionally, levels of an anti-Glc (α 1, 2) Gal (β) (GAAB) antibody IgM isotype antibody are detected.

At stage 126, the level of at least one antibody in the test sample is compared to one or more reference levels. Optionally, a computer or computer network is used to make the comparison. For example, the reference levels are stored on a computer-readable medium associated with computer or computer network, and the patient's at least one antibody level is received via an input device (e.g., keyboard, GUI, COM port).

At stage 128, the patient's risk factor for developing breakthrough MS is determined. For example, if the level of at least one of the antibodies in the test sample is higher than a reference level, then the patient is at higher risk of developing breakthrough MS. In an embodiment, a computer can be used to generate an output (e.g., report, message, display) to indicate the corresponding risk factor.

Other Embodiments

While the invention has been described in conjunction with the detailed description thereof, the foregoing description is intended to illustrate and not limit the scope of the invention, which is defined by the scope of the appended claims. Other aspects, advantages, and modifications are within the scope of the following claims.

The patent and scientific literature referred to herein establishes the knowledge that is available to those with skill in the art. All United States patents and published or unpublished United States patent applications cited herein are incorporated by reference. All published foreign patents and patent applications cited herein are hereby incorporated by reference. Genbank and NCBI submissions indicated by accession number cited herein are hereby incorporated by reference. All other published references, documents, manuscripts and scientific literature cited herein are hereby incorporated by reference.

While this invention has been particularly shown and described with references to preferred embodiments thereof, it will be understood by those skilled in the art that various changes in form and details may be made therein without departing from the scope of the invention encompassed by the appended claims.

What is claimed is:

1. A method of identifying a subject with relapsing-remitting multiple sclerosis (RRMS) who is at risk for an active disease course as measured by contrast-enhancing T1 MRI lesions, the method comprising:
   providing a test sample from said subject;
   measuring in said test sample the levels of an anti-Glc ($\alpha$ 1,2) Gal ($\beta$) (GAAB) IgM antibody; and
   comparing the levels of said antibody in said test sample to a reference level of said antibody, wherein a higher level of said antibody compared to the reference level of said antibody correlates with an active disease as measured by contrast-enhancing T1 MRI lesions.

2. The method of claim 1, wherein said test sample is a biological fluid selected from the group consisting of whole blood, serum, and plasma.

3. A method of identifying a subject with RRMS who will develop breakthrough MS, the method comprising:
   providing a test sample from said subject;
   measuring in said test sample the levels of an anti-Glc ($\alpha$ 1,2) Gal ($\beta$) (GAAB) IgM antibody; and
   comparing the levels of said antibody in said test sample to a reference level of said antibody, wherein a higher level of said antibody compared to the reference level of said antibody correlates with breakthrough MS.

4. The method of claim 3, wherein said test sample is a biological fluid selected from the group consisting of whole blood, serum, or plasma.

* * * * *